United States Patent [19]
Cohen

[11] Patent Number: 5,817,005
[45] Date of Patent: *Oct. 6, 1998

[54] APPARATUS AND METHOD FOR SIMULTANEOUSLY RETRACTING AND VIEWING BODILY TISSUES

[76] Inventor: Barry J. Cohen, 11618 Yeatman Ter., Silver Spring, Md. 20902

[*] Notice: The term of this patent shall not extend beyond the expiration date of Pat. No. 5,584,796.

[21] Appl. No.: 767,377

[22] Filed: Dec. 16, 1996

Related U.S. Application Data

[63] Continuation of Ser. No. 292,812, Aug. 10, 1994, Pat. No. 5,584,796.

[51] Int. Cl.⁶ .................................................. A61B 1/22
[52] U.S. Cl. ..................... 600/201; 600/223; 600/188; 600/199; 600/245
[58] Field of Search .................................. 600/201, 212, 600/223, 187, 188, 199, 205, 241, 181, 116, 207, 156, 178, 182, 245, 248, 249, 191, 160; 433/29; 362/32, 251, 257

[56] References Cited

U.S. PATENT DOCUMENTS

| | | |
|---|---|---|
| D. 312,306 | 11/1990 | Michelson . |
| 3,626,471 | 12/1971 | Florin . |
| 4,049,000 | 9/1977 | Williams . |
| 4,226,228 | 10/1980 | Shin et al. . |
| 4,384,570 | 5/1983 | Roberts . |
| 4,562,832 | 1/1986 | Wilder et al. . |
| 4,608,965 | 9/1986 | Anspach, Jr. et al. . |
| 4,794,912 | 1/1989 | LIa . |
| 4,872,446 | 10/1989 | Murata . |
| 5,035,232 | 7/1991 | Lutze et al. . |
| 5,039,198 | 8/1991 | Van Beek . |
| 5,109,276 | 4/1992 | Nudelman et al. . |
| 5,123,403 | 6/1992 | Lavyne . |
| 5,159,446 | 10/1992 | Hibino et al. . |
| 5,159,921 | 11/1992 | Hoover . |
| 5,222,477 | 6/1993 | LIa . |
| 5,337,732 | 8/1994 | Grundfest et al. . |
| 5,584,796 | 12/1996 | Cohen ..................................... 600/201 |

*Primary Examiner*—Beverly M. Flanagan
*Attorney, Agent, or Firm*—Thelen Reid & Priest LLP

[57] ABSTRACT

A retractor device for simultaneously retracting and viewing bodily tissues during a medical procedure. The retractor includes a blade member for retracting bodily tissues and an imaging device to form an image of the bodily tissues which are exposed by the operation of the blade member. The imaging device is coupled to a display device so that the image of the bodily tissues formed by the imaging device is displayed by the display device. Moreover, a method is provided for endoscopically performing a tissue retracting procedure using a retractor device. The method includes the steps of retracting bodily tissues using a retractor to form a cavity and imaging the cavity using an imaging device mounted on said retractor to form an image of the cavity and to provide the image of the cavity to a display device that is coupled to the imaging device.

8 Claims, 4 Drawing Sheets

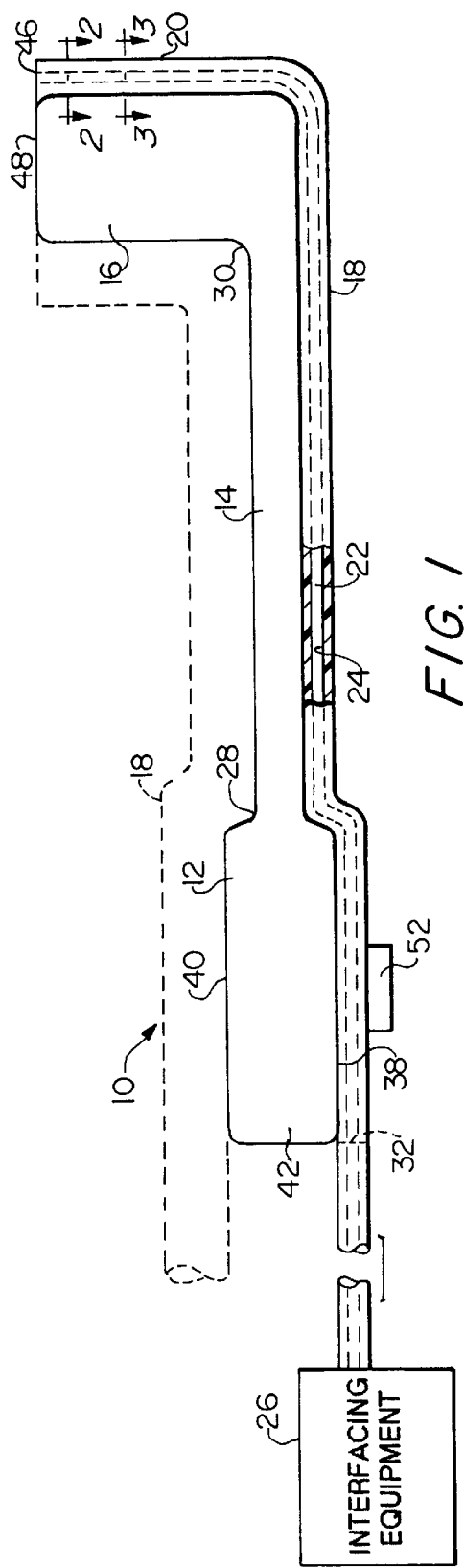
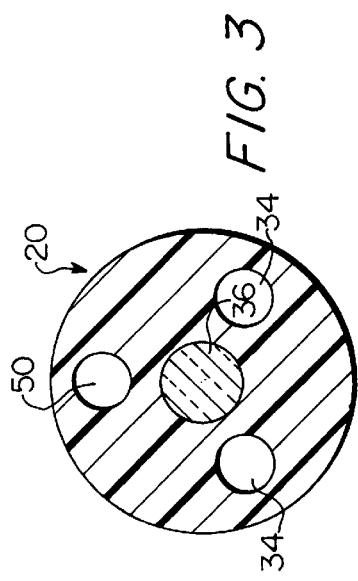
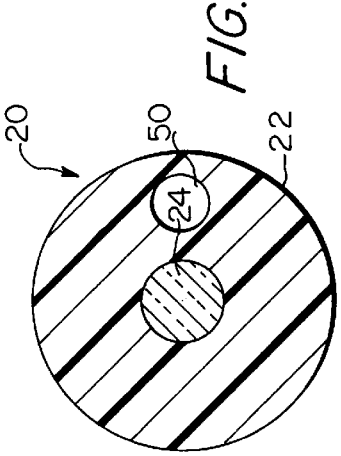

APPARATUS AND METHOD FOR SIMULTANEOUSLY RETRACTING AND VIEWING BODILY TISSUES

This is a continuation of U.S. application Ser. No. 08/292,812, filed Aug. 10, 1994, now U.S. Pat. No. 5,584,796.

BACKGROUND OF THE INVENTION

1. Field of the Invention

The present invention relates to a surgical implement, and more particularly, to a surgical implement used to simultaneously retract and view bodily tissues. Even more particularly, the invention relates to an endoscopic retractor equipped with an imaging unit to form images of bodily tissues which are exposed from operation of the endoscopic retractor.

2. Description of the Related Art

Many surgical procedures done today typically include the use of an endoscopic device to aid surgeons and medical staff to visualize bodily tissues exposed during a surgical procedure. An endoscopic procedure may even be carried out to merely view bodily tissues (e.g., a colonoscopy). Basically, an endoscope is inserted through the skin of a patient into a prepared opening in the body which is typically called a cavity. The cavity is often filled with air or other gasses to expand the cavity for better viewing. See U.S. Pat. No. 4,608,965 to Anspach, Jr., et al. The '965 patent teaches an endoscope retainer that does not slip out of a cavity and also retracts soft tissue around the opening in the cavity away from the cavity to provide a better view of the cavity.

Typically, the endoscopes of the type contemplated herein, include a probe part which is inserted into an bodily organ. Generally, the probe part includes a charge coupled device (CCD) on its end to form images of the object of interest (e.g., a heart or other bodily organ), an illuminating member such as light channel to supply light to the object of interest, a lens though which the CCD captures a reflection of the light illuminated by the illuminating member from the object of interest and a receiving channel member to receive and transmit the electric signals produced by the CCD to a main system which converts the electric signals into image signals (e.g., NTSC signals or other signals which are displayable on a television tube device or on another type of cathode ray device—e.g., a computer terminal screen). See e.g., U.S. Pat. No. 4,872,446 to Nudelman et al.. The '446 patent, in particular, discloses a probe carrying a single fiber optics channel including a flexible coherent fiber optics bundle for both transmitting illumination light and receiving reflected light from the object. An endoscope of such a configuration can be used in very small diameter applications, such as those required in the imaging of coronary arteries.

Procedures currently being done with an endoscope include gall bladder surgery, knee surgery, hernia surgery, insertion of breast implants through a long tube through the navel, brow lift surgery, and colon resection. Additionally, OB/GYN surgeons have been using endoscopy for many years to treat various problems of the pelvic area. Orthopedic surgeons use endoscopic procedures to and access joint cavities.

The benefits which result from using an endoscope are not, however, available to all types of medical procedures. This is because many procedures that exist today and that require a relatively small opening of the skin of a subject to allow for direct visualization and/or insertion of implantable material are not being done endoscopically due to the delicate nature of the procedure. For example, in breast augmentation in women, an incision of approximately 3 to 4 centimeters (cm) is made under a women's breast. Through this relatively small incision, a relatively large implant needs to be inserted into an even larger pocket, which pocket needs to be created through the small incision. To help facilitate this type of procedure, there are currently available lighted retractors. See e.g., U.S. Pat. No. 4,226,228 to Shin et al. and U.S. Pat. No. 5,035,232 to Lutze et al..

Generally, a retractor is a hand-held rod-like structure which is curved in such a way as to allow a surgeon to pull tissue away from an incision in order to open the incision to provide for direct visualization of the operative sight or location. A surgeon may more easily visualize the pocket with a lighted retractor of the type contemplated above. However, problems still exist when visualizing deep pockets. For example, the operating surgeon often must contort her body and neck in order to strain to see the depths of the wound made by a relatively small incision. A surgeon often encounters similar problems when doing face lifts, particularly in the area of the neck.

U.S. Pat. No. 5,039,198 to VanBeek attempts to alleviate some of the problems mentioned above with a stereoscopic microsurgery system. In the system of the '198 patent, a head mounted viewing assembly, including dual optical viewers, is used for depth of field viewing of an operative sight or location. Problematically, however, the system of the '198 patent is bulky and inconvenient to use and it does not provide a clear and complete view of the operative site as would and imaging device of the type used in endoscopes.

SUMMARY OF THE INVENTION

In view of the foregoing and other problems associated with the art to which the present invention relates, it is therefore an object of the present invention to solve such problems.

It is yet a further object of the present invention to provide a surgical implement for easily and clearly visualizing a bodily cavity formed through a relatively small opening in a skin surface.

It is still another object of the present invention to provide a single surgical implement for simultaneously performing a minimal opening tissue retracting procedure and providing endoscopic visualization of a pocket formed through a relatively small incision made as a result of the minimal opening procedure.

It is yet a further object of the present invention to provide a single surgical implement for performing a minimal opening tissue retracting procedure, simultaneously providing endoscopic visualization of a deep pocket formed through a relatively small incision made by the minimal opening procedure and also simultaneously providing suction to evacuate smoke and other matter (e.g., gasses or liquids) which are produced by an electrocautery device.

It is still a further object of the present invention to enable assistants of an operating surgeon to easily and clearly visualize an operative site while the surgeon performs a tissue retracting procedure.

It is still another object of the present invention to facilitate teaching a tissue retracting procedure.

It is still a further object of the present invention to reduce the number of instruments, and therefore the number of hands, required to perform a given surgical procedure.

These and other objects of the present invention are achieved by providing a retractor device for simultaneously retracting and viewing bodily tissues during a medical procedure. The retractor includes a blade member for retracting bodily tissues and an imaging device to form an image of the bodily tissues which are exposed from operation of the blade member. The imaging device is coupled to a display device so that the image of the bodily tissues is displayed thereby.

Moreover, the present invention provides a method for endoscopically performing a tissue retracting procedure using a retractor device. The method includes the steps of retracting bodily tissues using a retractor device to form a cavity and imaging the cavity using an imaging device mounted on said retractor to form an image of the cavity and to provide the image of the cavity to a display device that is coupled to the imaging device.

BRIEF DESCRIPTION OF THE DRAWINGS

The above-listed and other features and advantages of the present invention will become apparent and readily appreciated from the following detailed description of the preferred embodiments, taken in conjunction with the attached drawing figures, of which like elements are represented by like reference numerals and of which:

FIG. 1 is a top view of an endo-retracting device according to a first embodiment of the present invention;

FIG. 2 is a cross-sectional view of the endo-retracting device of FIG. 1 taken along the line 2—2;

FIG. 3 is a cross-sectional view of the endo-retracting device of FIG. 1 taken along the line 3—3.

DETAILED DESCRIPTION OF PREFERRED EMBODIMENTS

Figure 4:
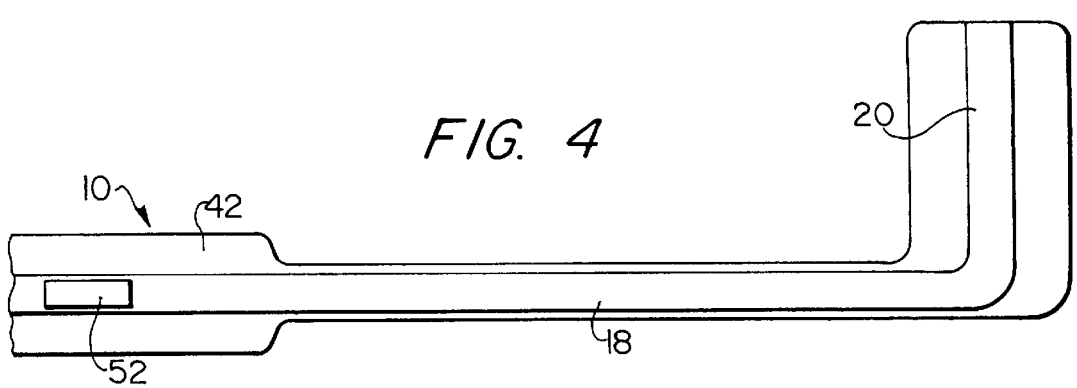
FIG. 4 illustrates a modification to the endo-retracting device of FIG. 1.
Figure 5:
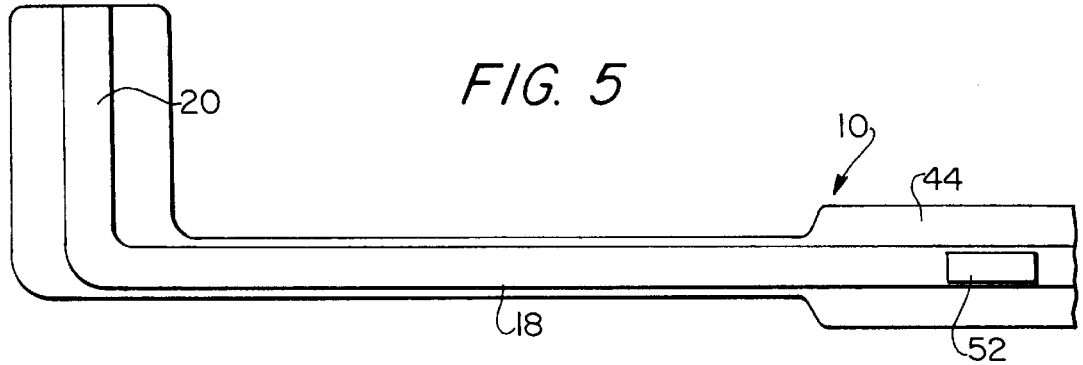
FIG. 5 illustrates a further modification to the endo-retracting device of FIG. 1.

The present invention is now described with regard to the exemplary embodiments shown in FIGS. 1–10. Like parts will be referred to with like reference numerals where appropriate within the drawings.

Figure 9:
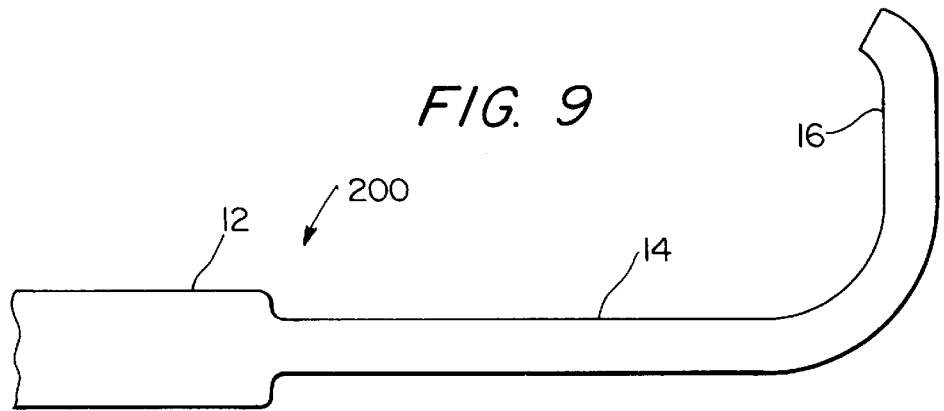
FIG. 9 illustrates an example of an alternative configuration of the retracting devices of the first, second and third embodiments depicted in FIGS. 1–8.

Referring now to FIG. 1, a preferred embodiment of a surgical implement in accordance with the present invention is designated generally by the reference numeral 10. Surgical implement 10 includes handle 12, shaft 14, blade 16 and endoscope 18. Elements 12, 14 and 16 form a conventional retractor of various configurations. With reference to FIG. 9, therein shown is an example of an alternative configuration of a conventional retractor. In particular, endoscope 18 includes scope (i.e. probe) 20, fiber-optics bundle 22 disposed within fiber-optics channel 24 and standard interfacing equipment 26 for receiving and processing signals from the fiber-optics bundle and displaying an image based on the received and processed signals under the display device of the interfacing equipment. Shaft 14 has a first end portion 28 and a second end portion 30. Handle 12 is rigidly and integrally formed with shaft 14 at first end portion 28. Blade 16 is rigidly and integrally formed with shaft 14 at second end portion 30. Retracting elements 12, 14 and 16 are preferably made from a rigid material such as metal, but may be made from other materials such as hard plastics, rubber or the like. All that is required of the material from which retracting elements 12, 14 and 16 are formed is that such material be suited to surgical uses.

Endoscope 18 is shown as being encased with a strong plastic or metal material to withstand sterilization techniques, i.e., an autoclave, along with retractor elements 12, 14 and 16. Endoscope 18 may be disconnected from equipment 26 at approximately 32 for sterilization and storage. Scope 20 is insertable into a body cavity along with blade 16 and a top surface 46 of scope 20 is approximately even with a top surface 48 of blade 16. Scope 20 has a conventional internal configuration, such as that disclosed in the Nudelman et al. or the Murata patent as such were mentioned above. That is, referring now to FIG. 2, which illustrates a cross sectional view taking along the line 2—2 of FIG. 1, scope 20 includes a signal fiber-optics channel 24 containing fiber-optics bundle 22, as disclosed in Nudelman et al..

It should be noted that with regard to the embodiment shown in FIG. 1 and with regard to the other embodiments discussed herein, that the endoscope part of the retractor device is configured to form images of bodily tissues. In particular, the endoscope should be configured to generate electrical signals which can be processed to form image or video signals for display on a display device. For example, an endoscope can be used which generates television (TV) signals which can be processed in conventional ways to be displayed on a television set or monitor. For a discussion of the use of cameras and fiber-optic bundles to achieve the video-optical characteristics of the endoscope and its features of the present invention, the reader is directed to the above-mentioned Nudelman et al. patent (U.S. Pat. No. 5,109,276). Additionally, it should be noted that the signals generated by the endoscope structure of the present invention can be digitally processed to aid in visualizing special image characteristics and like (e.g., visually detecting radioactive coloring agents in bodily tissues). Such digital processing techniques for television and video signals are generally discussed in R. H. Stafford, *DIGITAL TELEVISION (Bandwidth Reduction and Communication Aspects)*, John Wiley & Sons Press, Copyright 1980.

With reference now to FIG. 3 on the other hand, which illustrates a cross-sectional view taking along the line 3—3 of FIG. 1, scope 20 includes at least one illuminating channel 34 in a receiving channel 36 including a lens (not shown) and a CCD device (not shown) for transmitting light reflected from an object, as disclosed in Murata.

Referring again to FIG. 1, endoscope 18 is arranged along either side (the opposite side illustrated by broken lines) of retractor elements 12, 14 and 16, along the longitudinal direction of the retractor elements. Endoscope 18 is securely adhered to the retractor elements along surface 38 (or surface 40) with conventional bonding techniques such as glue. Instead, endoscope 18 may be securely connected to the retractor elements with conventional connecting elements such a screws or clamps (not shown). Similarly, endoscope 18 may be adhered or connected to a top surface 42 (see FIG. 4) or a bottom surface 44 (see FIG. 5) of the retractor elements. Referring again to FIGS. 1, 2 and 3, surgical implement 10 may further include a suction tube 50 located within endoscope 18, to simultaneously evacuate smoke produced by an electrocautery device while retracting tissue with implement 10.

FIG. 1 further shows a knob or joystick 52 attached to the endoscope near the handle, to allow the surgeon to control a rotation of scope 20 to adjustably visualize the entire cavity while gripping handle 12 and retracting tissue. See e.g., the Murata patent which teaches a control knob for controlling vertical and horizontal movements of a head portion of a probe. See also, U.S. Pat. No. 5,159,466 to Hibino et al., which teaches a distal end of the endoscope provided with a bendable portion. Moreover, the Hibino et al. patent teaches both a knob for manually operating the bendable portion and a joystick for vertically and horizontally bending the bendable portion in conjunction with a motor. The Hibino et al. patent also teaches a straight switch for straightening the bendable portion and a vibration switch for minutely vibrating the bendable portion.

Figure 6:
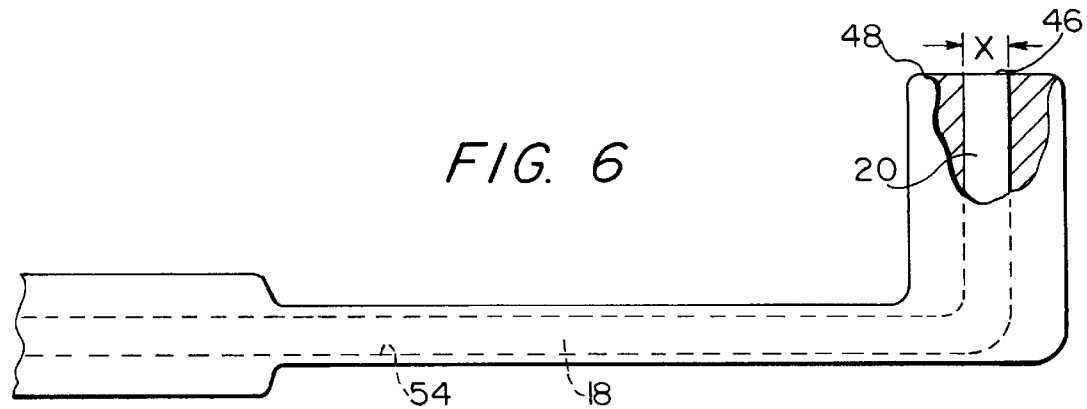
FIG. 6 is a top view of an endo-retracting device according to a second embodiment of the present invention.
Figure 7:
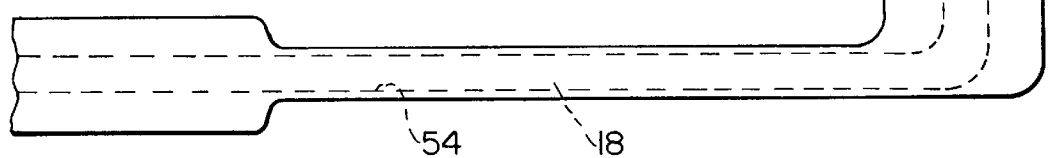
FIG. 7 illustrates a modification of the second embodiment depicted in FIG. 6.

With reference now to FIG. 6, therein illustrated is a second embodiment of a surgical implement 100 of the present invention. In this embodiment, endoscope 18 is located within hollow portion 54 of the retractor elements 12, 14 and 16. Hollow portion 54 runs through handle 12, shaft 14 and blade 16. Endoscope 18 fits securely within hollow portion 54 and includes the same channel(s) as illustrated in either FIGS. 2 or 3. Top surface 46 of the scope is aligned with the top surface 48 of blade 16. Top surface 46 of blade 16 is either transparent to allow imaging by scope 20 or has an aperture of width X equal to the width of scope 20 or the width of channel 54, to allow imaging by scope 20. FIG. 7 shows scope 20 slightly above top surface 48 of blade 16, such that scope 20 protrudes slightly from aperture X. The surgical implement 100 of the embodiment shown in FIG. 6, as well as the modification to second embodiment shown in FIG. 7, may further include knob/joystick 52, attached to an outer surface of handle 12 and internally to endoscope 18 to control a movement of probe 20 as discussed above with regard to the first preferred embodiment. As further discussed above, implement 100 of FIGS. 6 and 7 may additionally include a suction channel and illuminating channel within endoscope 18.

Figure 8:
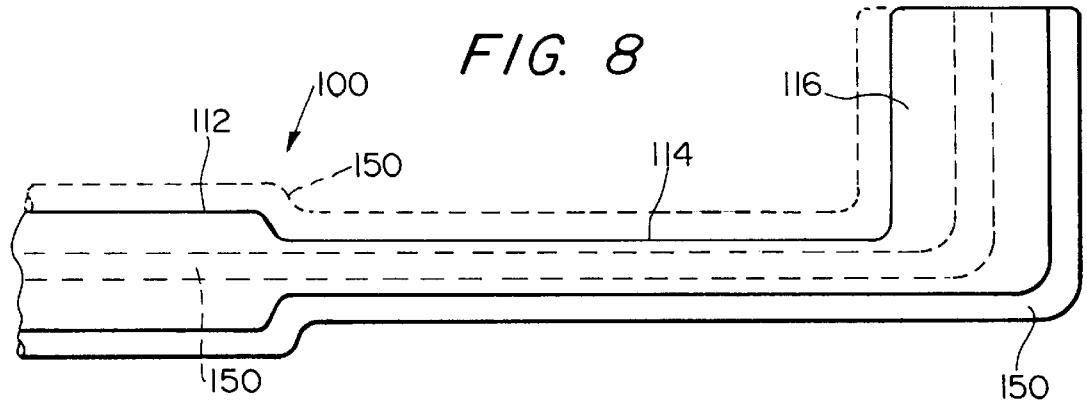
FIG. 8 is a top view of a suction-retracting device according to a third embodiment of the present invention.

With reference now to FIG. 8, therein depicted is a third embodiment of a surgical implement, in accordance with the present invention and is designated generally by reference numeral 200. Similar to the embodiment of FIG. 1, surgical implement 200 includes handle 12, shaft 14, blade 16 and suction channel 50. Elements 12, 14 and 16 form a conventional retractor of various configurations. Suction channel 50 may be connected to either side of the retractor elements, similar to the endoscope of FIG. 1, or may be connected on either the top or bottom surface of the retractor elements, similar to the endoscope of FIGS. 4 and 5. The retractor is a conventional lighter retractor in combination with a suction device. Alternatively, suction channel 50 may be located within the hollow portion 54 of the retractor, similar to the endoscope of FIG. 6, with the hollow portion also including a conventional illumination channel. The embodiment of FIG. 8 illustrates a hand held retractor and a suction device to facilitate the suction of smoke of a tissue retraction operation that a accumulates in a large pocket with a small opening.

Figure 10:
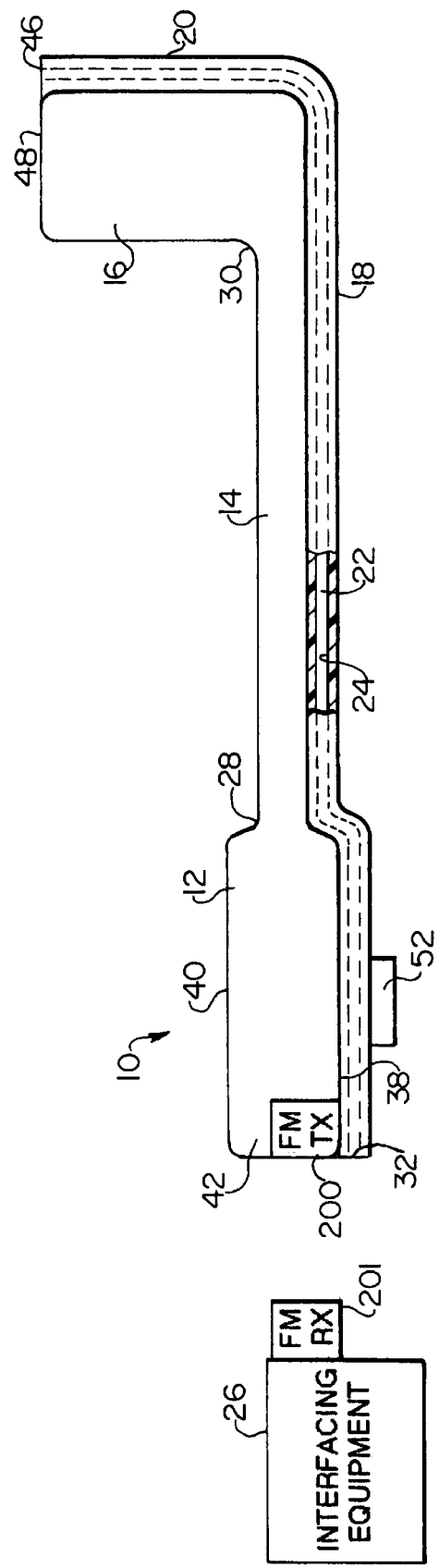
FIG. 10 illustrates a fourth embodiment according to the present invention which employs a wireless signal transmission system.

Referring now to FIG. 10, therein depicted is yet another embodiment of the present invention. For the most part, this embodiment is exactly the same as the embodiment depicted in FIG. 1. However, the embodiment depicted in FIG. 10 employs commonly used and understood wireless transmission technology to transmit a video or other signal(s) form a transmitter 200 located on surgical implement 10 to corresponding receiver 201. The signals transmitted by transmitter 200 and which are received by receiver 201 can processed by interfacing equipment 26 and displayed in a conventional manner. For example, if the transmitter 200 is configured to process a video signal of the television variety (i.e., a raster type signal which originates from detections by a CCD type device and which are converted to an NTSC signal) such a signal may then be transmitted by well-known and used FM radio transmission devices to receiver 201 for processing so that interface equipment 26 can display the same in a conventional way. A typical wireless video signal transmission system comprising a transmitter for processing a video signal to produce an FM radio broadcast in the FM radio range of about 900 Mhz which can be received by a corresponding radio receiver is one manufactured by RECOTON Corporation having Model No. V900SX. The V900SX system is designed so that a video source (e.g., a NTSC video source) connects to a transmitter which transmits FM broadcasts at either 914 or 922 Mhz and which are received by receiver which is typically connected to a video signal display device (e.g., a television set or monitor).

It is believed that the use of such wireless systems within the context of the present invention and, in particular, the embodiment depicted in FIG. 10, will now allow surgeons to effectively use an endo-scopic retracting device without having to be burdened with messy wire and cable arrangements which are typically referred to a "spaghetti wires." That is, the embodiment depicted in FIG. 10 will now allow surgeons to have a single, hand-held endo-scopic retracting device which is free of any tethering device such as a cable which connects the device to a display system. The details of coupling a radio or other wireless signal transmitter to a corresponding radio or wireless signal receiver in the context of the present invention will be readily appreciated by those skilled in the art of wireless signal transmission systems. Moreover, while enabling disclosure has been provided with reference to FM or radio based transmission systems, other forms of wireless transmission systems (e.g., Infra-Red, etc.) can be employed. Finally, it should be noted that in the case of the embodiment depicted in FIG. 10, power systems such as batters or the like would need to be maintained within implement 10 so as to provide operational energy to the components of the imaging system and the signal transmission system; such power and battery systems, especially in the field of medical devices, are well known to those skilled in the art of medical electronic devices.

Although a few preferred embodiments of the invention have been shown and described, it will be readily appreciated by those skilled in the art that many changes and modifications may be made to such embodiments without departing from the principles and spirit and scope of the present invention, the scope of which is defined in the appended claims.

What is claimed is:

1. A device for endoscopically performing a tissue retracting procedure, said device comprising:

a retractor having a handle connected to a shaft that is connected to a blade that is insertable into a body cavity to retract tissue;

a hollow portion formed as part of said retractor;

an endoscope dimensioned to fit securely within said hollow portion, said endoscope including capture means for capturing images of tissue being retracted and signal means for producing a signal corresponding to the captured images; and a remote display device connected to said signal means for displaying the captured images based on said signal.

2. The device as claimed in claim 1, further comprising a knob connected to said endoscope and located adjacent said handle of said retractor, to adjustably control a movement of said endoscope through a plurality of viewing angles within with body cavity.

3. The device as claimed in claim 1, further comprising a suction tube connected to said blade, said shaft and said handle, to evacuate smoke produced by an electrocautery device and accumulated in the body cavity.

4. The retractor device according to claim 1, wherein said signal means and said remote display device are coupled via a cable.

5. The retractor device according to claim 1, wherein said signal means and said remote display device are coupled via a wireless transmission system.

6. The retractor device according to claim 5, wherein said wireless transmission system includes a transmitter for transmitting signals containing image information related to said catured image, said transmitter being mounted on said retractor device, said wireless transmission system further including a receiver coupled to said remote display device for receiving said signals and processing said signals so that said image information is displayed by said remote display device.

7. The retractor device according to claim 1, wherein said captured image is digitally processed prior to being displayed by said remote display device.

8. A method for simultaneously retracting and viewing bodily tissues during a medical procedure, the method comprising the following steps:

retracting bodily tissues using a retractor having a blade member to form a cavity;

imaging said cavity using an imaging device mounted on said retractor to an image of said cavity, said imaging device being coupled to a display device so that said image of said cavity is displayed by said display device.

* * * * *